United States Patent
Adams et al.

(10) Patent No.: US 9,440,062 B2
(45) Date of Patent: Sep. 13, 2016

(54) MEDICAL SITE COVER

(71) Applicants: Kyle S. Adams, Dallas, TX (US); Gordon E. Atkinson, Black Mountain, NC (US)

(72) Inventors: Kyle S. Adams, Dallas, TX (US); Gordon E. Atkinson, Black Mountain, NC (US)

(73) Assignee: iMed Technology, Inc., Dallas, TX (US)

( * ) Notice: Subject to any disclaimer, the term of this patent is extended or adjusted under 35 U.S.C. 154(b) by 110 days.

(21) Appl. No.: 14/228,859

(22) Filed: Mar. 28, 2014

(65) Prior Publication Data

US 2015/0273199 A1 Oct. 1, 2015

(51) Int. Cl.
*A61M 39/16* (2006.01)
*A61M 39/20* (2006.01)
*A61M 39/02* (2006.01)

(52) U.S. Cl.
CPC ........... *A61M 39/16* (2013.01); *A61M 39/165* (2013.01); *A61M 39/20* (2013.01); *A61M 2039/0205* (2013.01); *A61M 2039/027* (2013.01); *A61M 2039/0258* (2013.01); *A61M 2039/0285* (2013.01); *A61M 2039/0288* (2013.01)

(58) Field of Classification Search
CPC .... A61J 1/1412; A61J 1/1418; A61J 1/1425; A61M 2039/027; A61M 39/02; A61M 2039/0285; A61M 2039/0288
See application file for complete search history.

(56) References Cited

U.S. PATENT DOCUMENTS

| | | | |
|---|---|---|---|
| 3,315,830 A * | 4/1967 | Flynn | B65D 41/0492 215/334 |
| 4,440,207 A | 4/1984 | Genatempo et al. | |
| 4,597,758 A * | 7/1986 | Aalto | A61M 39/20 139/178 |
| 5,554,135 A | 9/1996 | Menyhay | |
| 5,694,978 A | 12/1997 | Heilmann et al. | |
| 6,632,199 B1 * | 10/2003 | Tucker | A61M 5/3134 604/192 |
| 7,214,214 B2 | 5/2007 | Sudo et al. | |
| 7,282,186 B2 | 10/2007 | Lake, Jr. et al. | |
| D607,325 S | 1/2010 | Rogers et al. | |
| 7,682,561 B2 | 3/2010 | Davis et al. | |
| 7,780,794 B2 | 8/2010 | Rogers et al. | |
| 7,931,877 B2 | 4/2011 | Steffens et al. | |
| 7,985,302 B2 | 7/2011 | Rogers et al. | |
| 8,065,773 B2 | 11/2011 | Vaillancourt et al. | |
| 8,206,514 B2 | 6/2012 | Rogers et al. | |
| 8,231,587 B2 | 7/2012 | Solomon et al. | |
| 8,328,767 B2 | 12/2012 | Solomon et al. | |
| 8,343,112 B2 | 1/2013 | Solomon et al. | |
| 8,480,968 B2 | 7/2013 | Lynn | |
| 8,491,546 B2 | 7/2013 | Hoang et al. | |
| 8,506,538 B2 | 8/2013 | Chelak | |
| 8,523,830 B2 | 9/2013 | Solomon et al. | |
| 8,523,831 B2 | 9/2013 | Solomon et al. | |
| 2008/0147047 A1 | 6/2008 | Davis et al. | |
| 2009/0028750 A1 | 1/2009 | Ryan | |
| 2010/0064456 A1 * | 3/2010 | Ferlic | A61L 2/235 15/104.94 |
| 2010/0306938 A1 | 12/2010 | Rogers et al. | |
| 2011/0232020 A1 | 9/2011 | Rogers et al. | |
| 2011/0265825 A1 | 11/2011 | Rogers et al. | |
| 2012/0111368 A1 | 5/2012 | Rahimy et al. | |
| 2012/0216359 A1 | 8/2012 | Rogers et al. | |
| 2012/0302997 A1 | 11/2012 | Gardner et al. | |
| 2013/0019421 A1 | 1/2013 | Rogers et al. | |
| 2013/0030414 A1 | 1/2013 | Gardner et al. | |
| 2013/0035667 A1 | 2/2013 | Anderson et al. | |

* cited by examiner

*Primary Examiner* — Bradley Osinski
(74) *Attorney, Agent, or Firm* — Stevens & Showalter LLP

(57) ABSTRACT

A medical site cover for a needle-free intravenous connector having a septum area and external threads. The medical site cover includes an elastomeric cap having an opening to an inner cavity. The inner cavity includes a first chamber adapted for receiving and surrounding the connector and a second chamber located between the first chamber and a closed end of the cap. A compressible member formed of an absorbent material is located in the second chamber, wherein the compressible member is a sphere.

22 Claims, 3 Drawing Sheets

MEDICAL SITE COVER

FIELD OF THE INVENTION

The present invention relates to protective caps for medical sites and, in particular, relates to protective caps that can be retained on medical sites, including medical connectors or ports, to isolate the sites from contaminants and to disinfect the sites.

BACKGROUND OF THE INVENTION

Needle-free intravenous ports and connectors allow repeated infusions of fluids into a patient's bloodstream without the need to reinsert a needle into the patient's skin each time. The ports typically include a septum mounted to an end of a housing, such as a conventional luer housing, to provide medical personnel a relatively simple means of introducing medicinal agents into the bloodstream without requiring repetitive needle injections. However, use of these ports can create contamination problems as a result of providing an exposed surface that is contacted by an insertion device, i.e., a male luer taper, when a connection is formed on the port.

Accordingly, the use of needle-free intravenous connectors can result in an increase in the number of bloodstream infections that may be attributed to contamination of the connector at the time of the fluid infusion. This increase in the number of bloodstream infections can be attributed to contamination of the ports and/or connectors by airborne sources and also can be the result of direct handling of the components.

Various techniques and procedures have been proposed for preventing contamination of the port and/or for disinfecting or sterilizing the port. For example, medical practitioners use cleaning methods that typically involve the application of a disinfectant prep pad to the port's septum surfaces. A proper cleaning and disinfection procedure requires that the septum of the needle-free intravenous port be properly cleaned and disinfected by permitting adequate time for the antiseptic to kill microorganisms prior to accessing the needle-free intravenous port. However, it is difficult to ensure that consistent performance of the cleaning procedure is practiced each time the port is accessed.

Additionally, various cleaning and cap devices have been proposed for use with intravenous ports. Such cleaning and cap devices are typically small, on the order of the size of a luer connector, and can present certain tactile challenges during handling and installation on the port.

SUMMARY OF THE INVENTION

In accordance with an aspect of the invention, a medical site cover is provided for a needle-free intravenous connector having a septum area and external threads. The medical site cover comprises a cap having an opening to an inner cavity. The inner cavity includes a first chamber adapted for receiving and surrounding the connector and a second chamber located between the first chamber and a closed end of the cap. A compressible member formed of an absorbent material is located in the second chamber, wherein the compressible member is a sphere.

A disinfectant agent can be provided in the absorbent material.

A lip can be formed at an inner end of the first chamber, the lip defining a diameter that is less than a diameter of the first chamber.

The second chamber can be configured with a curved wall defining a section of a sphere having a radius that is the same as a radius of the compressible member, and the second chamber may terminate at the lip.

The second chamber can have a volume that is greater than $(4/6)\pi r^3$ where r is the radius of the compressible member.

The compressible member may include a portion, defined by a continuation of the sphere, that extends past the lip into the first chamber.

The cap may be formed of an elastomeric material. The first chamber may be defined by an inner wall of the cap that is smooth for engaging in deforming contact around external threads on a connector. The cap may be flexible to elastically deform the second chamber and the compressible member by application of an elastic deformation force on an outer surface of the cap. A rib may extend circumferentially on an outer surface of the cap at a location adjacent to the opening to the inner cavity, wherein the rib defines a maximum dimension of the cap in a direction perpendicular to the opening. An outer surface of the cap surrounding the first chamber may be cylindrical and an outer surface of the cap surrounding the second chamber may be spherical.

In accordance with another aspect of the invention, a medical site cover is provided for a needle-free intravenous connector having a septum area and external threads. The medical site cover comprises a cap formed entirely of an elastomeric material, and the cap has an opening to an inner cavity. The inner cavity includes a first chamber defined by a smooth inner wall adapted for receiving and surrounding the connector and a second chamber located between the first chamber and a closed end of the cap. A compressible member formed of an absorbent material is located in the second chamber, wherein the compressible member is a sphere, and a disinfectant agent is provided in the absorbent material.

The second chamber can be configured with a curved wall defining a section of a sphere having a radius that is the same as a radius of the compressible member.

The curved wall may terminate at a junction between the second chamber and the first chamber.

The compressible member may include a portion, defined by a continuation of the sphere, that extends past the lip into the first chamber.

The second chamber can have a volume that is greater than $(4/6)\pi r^3$ where r is the radius of the compressible member.

The cap may be flexible to elastically deform the second chamber and the compressible member by application of an elastic deformation force on an outer surface of the cap.

A rib may extend circumferentially on an outer surface of the cap at a location adjacent to the opening to the inner cavity, wherein the rib defines a maximum dimension of the cap in a direction perpendicular to the opening.

An outer surface of the cap surrounding the first chamber may be cylindrical and an outer surface of the cap surrounding the second chamber may be spherical.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

In accordance with aspects of the invention, a medical site cover is described that provides efficiencies in use with a needle-free intravenous connector and efficiencies in manufacturing (assembly) of the site cover. As will be described further below the site cover described herein can provide tactile characteristics that facilitate retention and controlled manipulation of the site cover when grasped by a user's fingers. The site cover further includes characteristics that facilitate external manipulation of the site cover for dispensing of a disinfectant solution from a compressible member that has been infused with the solution. Further, a configuration of the compressible member reduces an aspect of manufacturing complexity, permitting an improved efficiency in assembling the compressible member to a cap of the site cover.

Figure 1:
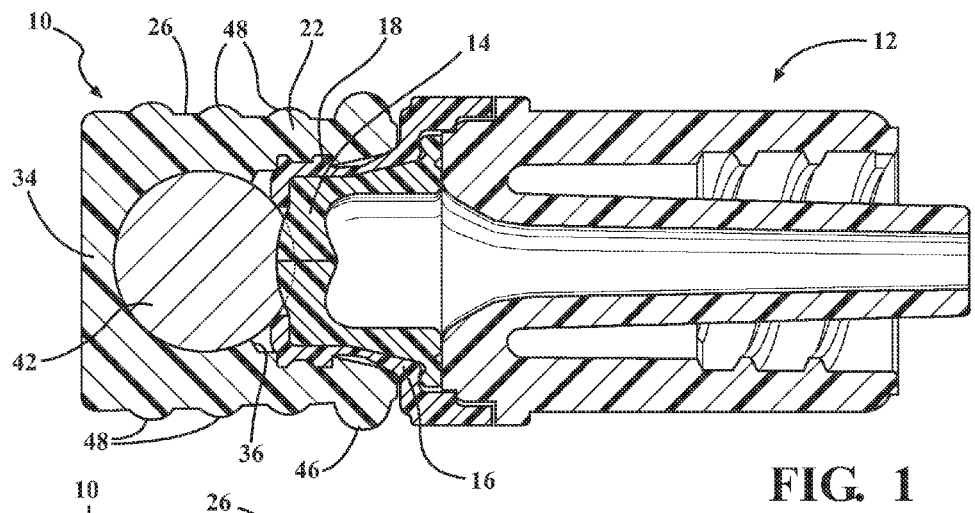
FIG. 1 is a cross-sectional view of a medical site cover illustrating aspects of the invention assembled to a needle-free intravenous connector.

Referring to FIG. 1, a medical site cover 10 is illustrated assembled to a needle-free intravenous connector or site 12 that defines a port configured to interface with a cooperating connector device during an infusion or other medical fluid transfer operation. For the purposes of the present description, the site 12 can be a known needle-free site comprising a septum 14 supported at the end of a housing 16 and configured for coupling with a standard male luer lock fitting (not shown). For example the site may be configured to receive a standard male luer taper constructing in accordance ANSI and ISO standards, having an outer diameter of about 3.9 mm to 4.0 mm and a threaded luer lock collar that has a minimum inner diameter, as defined by a thread portion, of about 7.0 mm to 7.2 mm. The site 12 can be conventionally formed with a thread or threads 18 configured to engage the thread of the luer lock collar. It may be understood that the particular site 12 illustrated herein is presented to provide a context for the description of the present site cover 10, and that the site 12 may be provided in other configurations than that specifically illustrated and described herein.

Referring to FIGS. 1-4, the medical site cover 10 includes a cap 20 that is formed entirely of an elastomeric material. The cap 20 includes a cylindrical wall 22 defined by a smooth cylindrical inner wall 24 and an outer wall 26 parallel to the inner wall 24. The inner wall 24 is located adjacent to an opening 28 to an inner cavity 30 of the cap 20, and the opening 28 is preferably defined at an inwardly tapered annular section of the inner wall 24.

Figure 3:
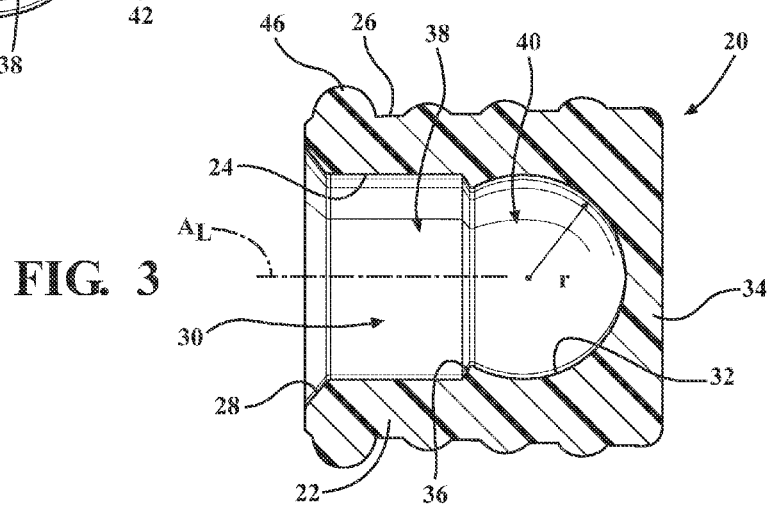
FIG. 3 is a cross-sectional view of a cap for the medical site cover of FIG. 1.

As may be seen with particular reference to FIG. 3, the cap 20 further includes a spherically curved inner wall 32 located between the cylindrical inner wall 24 and a closed end 34 of the cap 20. The spherical inner wall 32 defines a section of a sphere meaning that, although a portion of the inner wall 32 is defined as an interior surface of a sphere, it does not form an entire sphere, in that the inner wall 32 terminates at an intersection or junction with the cylindrical inner wall 24 at an annular lip 36. The annular lip 36 tapers radially inward from the cylindrical inner wall 24 and ends at an intersection with the spherical inner wall 32, such that the lip 36 defines a diameter that is less than the diameter of the inner cavity 30 defined by the inner wall 24. The area of the inner cavity 30 surrounded by the cylindrical inner wall 24 comprises a first chamber 38 of the inner cavity 30, and the area of the inner cavity 30 surrounded by the spherical inner wall 32 comprises a second chamber 40 of the inner cavity 30.

As used herein, the term "sphere" or "spherical" refers to a shape that is defined mathematically as the set of points that are all the same distance r from a given point in three-dimensional space. As noted above, the term "sphere" or "spherical" can also be used in reference to a portion of a sphere, that may also be referred to as a section of a sphere. In addition, reference to the term "ball" as used herein is intended to describe a spherical ball, i.e., as defined by the set of points that are all the same distance r from a given point in three-dimensional space, and may be used interchangeably with the term "sphere".

It should also be understood that, as used herein, "elastomer" or "elastomeric" refers to amorphous polymers existing above their glass transition temperature, and can include materials referred to as "thermoplastic elastomers". Further, as applied herein an "elastomer" is a polymer exhibiting the property of viscoelasticity, which also may be referred to as elasticity, and generally has a low Young's modulus and a high failure strain compared with other materials. The polymers of an elastomer comprise long polymer chains that are cross-linked by covalent cross-linkages. It may also be understood that the functional characteristics used in the present description, including the terms "flexible" and "elastic" or "elastically", are intended to specifically reference such functional aspects in the context of characteristics specifically associated with the elastomeric material. Further, as used herein, the elasticity referenced for the presently described structure can, in one instance, be characterized by the ability of opposing sides of the structure, i.e., the cap 20 described herein, to deform or move into engagement with each other, and return to its original shape, without a substantial permanent alteration of the material forming the structure, such as any alteration that would adversely affect future deforming movement of the structure and subsequent return to its original shape.

Figure 2:
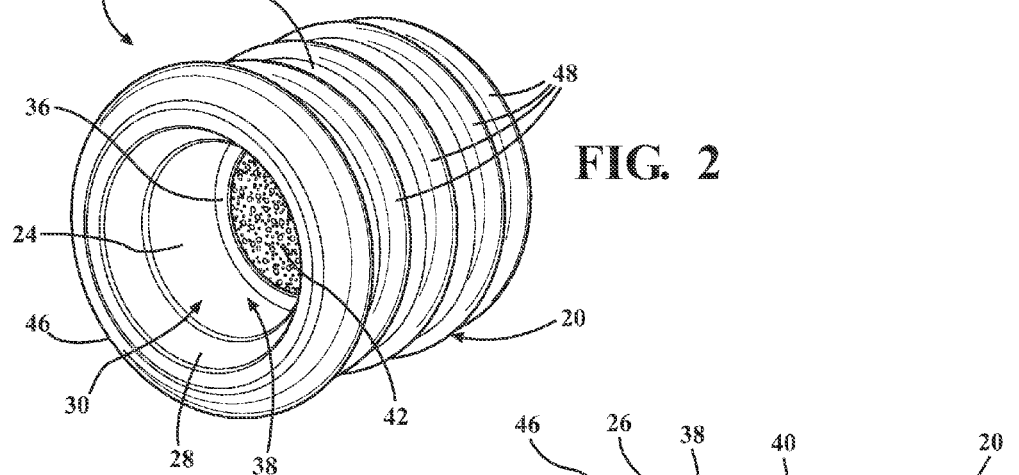
FIG. 2 is a perspective view of an entry end of the medical site cover of FIG. 1.
Figure 4:
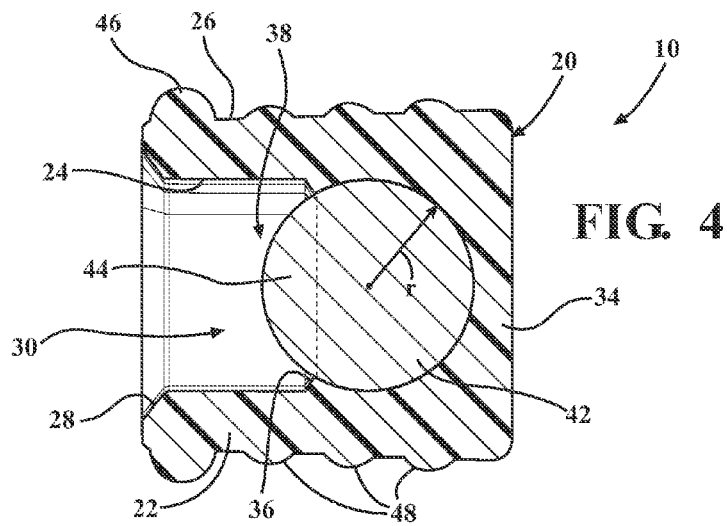
FIG. 4 is a cross-sectional view similar to FIG. 3 and including a spherical compressible member.

Referring to FIGS. 1, 2 and 4, the medical site cover 10 further includes a compressible member 42 formed of an absorbent material. The absorbent material may comprise, without limitation, any of a variety of materials capable of releasably retaining a solution to be dispensed by the compressible member 42. By way of example, the absorbent material may be a sponge material or a foamed polymer. The compressible member 42 can be provided with a disinfectant solution or agent for disinfecting and/or sterilizing the site 12. In particular, a solution comprising 70% isopropyl alcohol may be provided to the compressible member 42 for distribution to the end of the site 12, including the septum 14.

The compressible member 42 is formed in the shape of a sphere, i.e., is a spherical member or ball, having a radius r, and is located in the second chamber 40 in contact with the spherical inner wall 32. It should be noted that the radius r of the spherical compressible member 42 is the same as the radius r of the spherical inner wall 32. In a particular configuration of the invention adapted to be used in conjunction with a standard luer site 12, the sphere of the compressible member 42 may have a radius of 3 mm to 4.5 mm, i.e., a diameter of 6 mm to 9 mm.

In accordance with an aspect of the invention, the spherical compressible member 42 includes a portion 44, defined by a continuation of the sphere, that extends past the lip 36 into the first chamber 38. In order to ensure that the compressible member 42 is sufficiently surrounded by the material of the spherical inner wall 32, at least half of the compressible member should be located within the second chamber 40. That is, the second chamber 40 has a volume that is greater than half the volume of the compressible member 42, and the volume of the second chamber 40 can therefore be expressed as being greater than the quantity $(4/6)\pi r^3$. Further, it is preferable that about one-quarter of the surface area of the compressible member 42 is exposed and extends into the first chamber 38, providing a sufficient available area for engagement and compression against the end of the site 12 to provide an initial distribution of the disinfectant agent, while also providing a sufficient surface area of the inner wall 32 to surround and retain the compressible member 42 in the second chamber 40.

Figure 5:
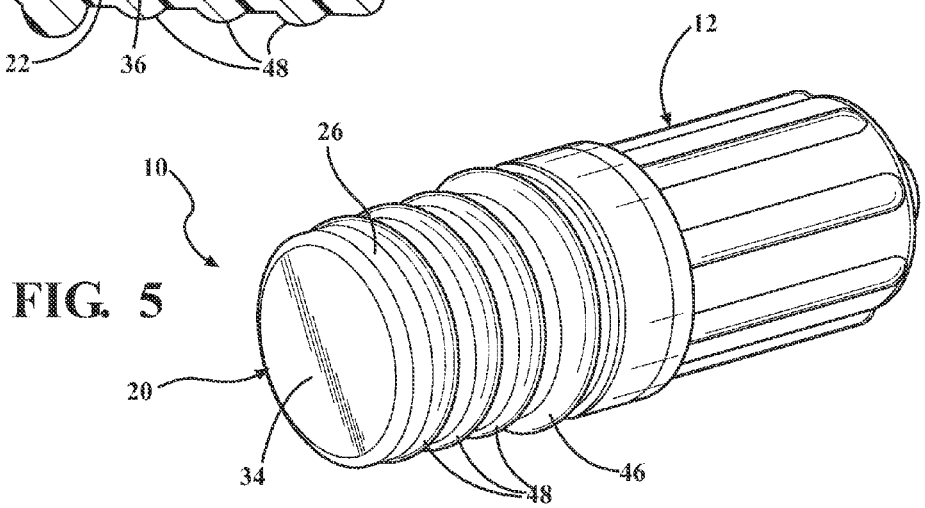
FIG. 5 is a perspective view of the medical site cover of FIG. 1 assembled to a needle-free intravenous connector.

FIGS. 1 and 5 illustrate the site cover 10 in position on the site 12. It can be seen that the inner wall 24 elastically deforms to conform to the shape of the site 12, including conforming around the threads 18 to effect a retention of the site cover 10 to the site 12. In this regard, it may be noted that the inner diameter of the inner wall 24 is less than an outer diameter on the site 12 defined by the threads 18, and it may be further noted that the site cover 10 is configured to slip onto the site 12 more easily than it is removed. An aspect of the invention providing this characteristic is an enlarged rib 46 extending circumferentially on the outer wall 26 of the cap 20 at a location adjacent to the opening 28 to the inner cavity 30, wherein the rib 46 defines a maximum dimension of the cap 20 in a direction perpendicular to the opening 28, i.e., in a plane perpendicular to a longitudinal axis $A_L$ (FIG. 3) of the first chamber 38. The rib 46 provides an enlarged area to push the end of the site cover 10 onto the site 12, and the thicker area of material provided by the rib provides a greater hoop tension for gripping the site 12.

The site cover 10 is provided with three additional circumferential gripping ribs 48 extending outward from the outer wall 26. The gripping ribs 48 facilitate retention of the relatively small site cover 10 in engagement with a user's fingers during installation of the site cover 10 on the site 12. In accordance with an aspect of the invention, it has been observed that prior devices for engagement with medical connection ports can inadvertently flip out of the user's fingers, and the present gripping ribs 48 provide engagement locations permitting control of the site cover 10 in the plane perpendicular to the longitudinal axis $A_L$, i.e., preventing or controlling rotation of the site cover 10 about an axis lying in a plane perpendicular to the longitudinal axis $A_L$. Further, the elastomeric material of the cap 20 allows the user's fingers to engage into the outer wall 26 in response to compression forces, and can avoid a reaction force that may result in the site cover 10 flipping out of the user's fingers.

In accordance with a further aspect of the invention, the elastomeric material of the cap 20 provides a dispensing function for increasing the dispensing of the disinfectant solution. In particular, the second chamber 40 is closely conformed around all adjacent areas of the spherical compressible member 42, and the cap 20 is flexible to elastically deform the second chamber 40 inward to deform the compressible member 42 by application of an elastic deformation force on an outer surface of the cap 20 by a user. In this regard, it should be noted that in accordance with an aspect of the invention the spherical shape of the compressible member 42 operates to increase the dispensing of the disinfectant solution. In particular, for a given compression of the spherical compressible member 42, a greater deflection of the compressible member can occur, with a greater dispensing of fluid, as compared to prior fluid dispensing devices that have been used, for example, cylindrical shaped dispensing elements and which have been located in rigid or similar inelastic structures.

It may be noted that the particular shape of the compressible member 42, i.e., as a spherical ball, can facilitate manufacturing efficiency of the present site cover 10. In particular, the spherical compressible member 42 can be dispensed or assembled to the interior cavity 30 of the cap 20 during an automated assembly operation without regard to an orientation of the compressible member 42, e.g. as compared to a cylindrical member. Hence, it is believed that assembly concerns associated with orientation, including potential misalignment of associated parts, can be avoided.

Figure 6:
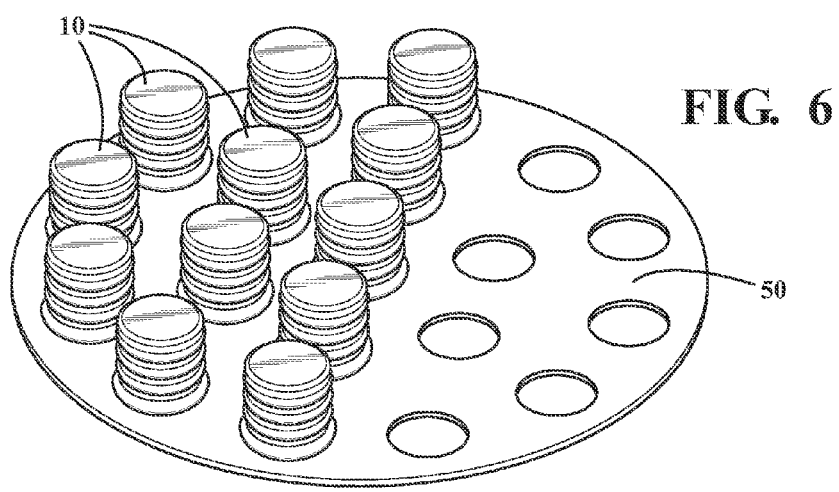
FIG. 6 is a perspective view showing a plurality of medical site caps supported on a card for dispensing from the card.

In a method of using the site cover 10, the site cover 10 may initially include a sealing membrane, such as a foil disk (not shown), adhered to the opening 28 to contain the disinfectant solution being held in the compressible member 42 and maintain sterility of the inner cavity 30 prior use. Alternatively, the site cover 10 could be provided on a card 50 (FIG. 6) with a plurality of other site covers 10 that are adhered to the card at their openings 28. The opening 28 of the site cover 10 can be uncovered and placed in engagement over the end of the site 12. The enlarged rib 46 can be pushed, such as by a user grasping the ribs 48 between the thumb and forefinger and pressing against the rib 48, to slide the site cover 10 past the threads 18 into full engagement with the site 12. When in full engagement with the site 12, the site 12 extends the full length of the first chamber 38 to the longitudinal location of the lip 36, placing the septum 14 in engagement with the portion 44 of the compressible member 42 and partially compressing the compressible member 42. The end of the site cover 10 surrounding the second chamber 40 can then be squeezed together to substantially compress the compressible member 42 therebetween and dispense the disinfectant solution to the site 12. It should be understood that by squeezing or compressing the site cover 10, substantially the entire quantity of disinfectant solution contained in the compressible member 42 can be dispensed onto the site 12.

The site cover 10 is provided to remain on the site 12 during times when the site 12 is not being accessed. Prior to accessing the site 12, the end of the site cover 10 can be compressed to dispense the disinfectant solution to perform a disinfecting operation. The site cover 10 may then be removed from the site 12 by bending or peeling, i.e., elastically flexing, the site cover 10 to flex the cylindrical wall 22 and disengage the inner wall 24 from the threads 18, and pulling the site cover 10 out of engagement with the site 12.

Figure 7:
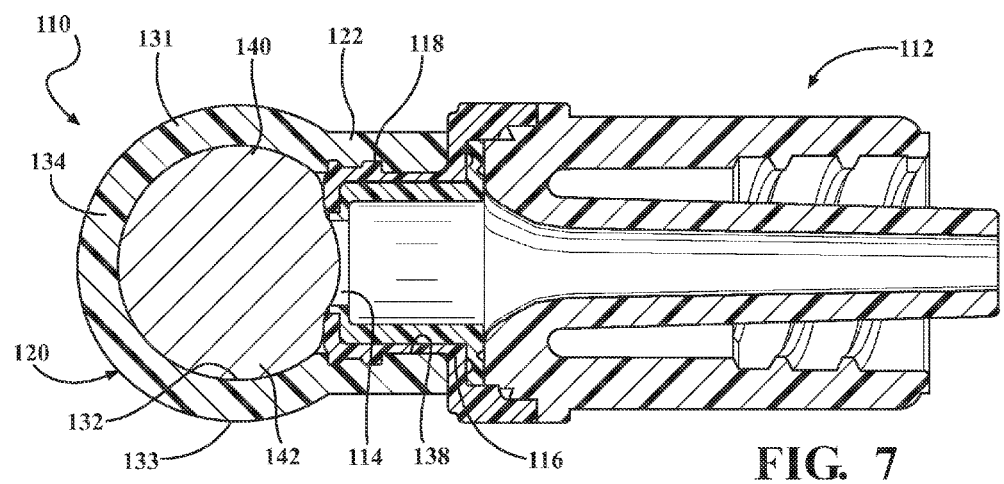
FIG. 7 is a cross-sectional view of an alternative configuration of a medical site cover, illustrating aspects of the invention, assembled to a needle-free intravenous connector.
Figure 8:
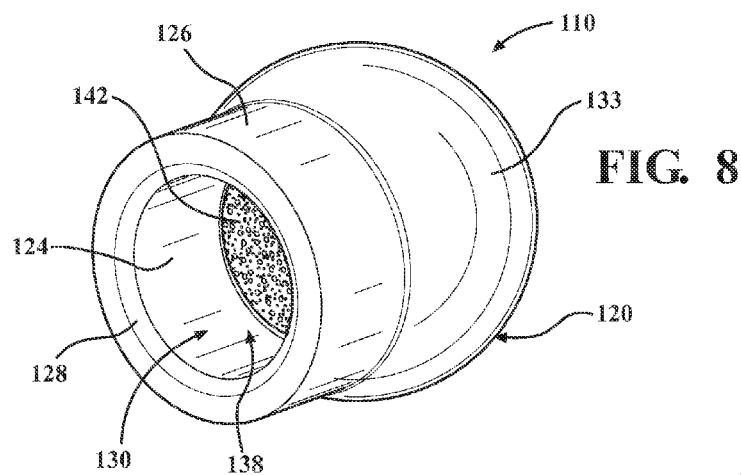
FIG. 8 is a perspective view of an entry end of the medical site cover of FIG. 7.
Figure 9:
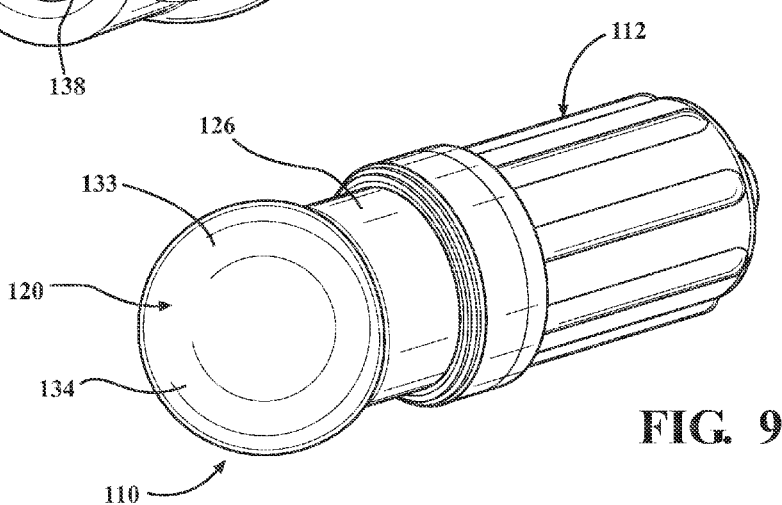
FIG. 9 is a perspective view of the medical side cover of FIG. 7 assembled to a needle-free intravenous connector.

Referring to FIGS. 7-9, an alternative configuration of a medical site cover 110 is illustrated, in which elements of the site cover 110 corresponding to the site cover 10 described with reference to FIGS. 1-4 are identified with the same reference numerals increased by 100.

Referring to FIG. 7, the medical site cover 110 is illustrated assembled to a needle-free intravenous connector or site 112 that defines a port to interface with a cooperating connector device during an infusion or other medical fluid transfer operation. The site 112 can be a known needle-free site comprising a septum 114 supported at the end of a housing 116 and configured for coupling with a standard male luer lock fitting (not shown), as described above with reference to the site 12 and associated site cover 10, and can include threads 118 configured to engage the threads of the luer lock collar.

The medical site cover 110 includes a cap 120 that is formed entirely of an elastomeric material. The cap 120 includes a cylindrical wall 122 defined by a smooth cylindrical inner wall 124 and an outer wall 126 parallel to the inner wall 124. The inner wall 124 is located adjacent to an opening 128 to an inner cavity 130 of the cap 120, and the opening 128 is preferably defined at an inwardly tapered annular section of the inner wall 124.

As may be seen with particular reference to FIGS. 7 and 8, the cap 120 further includes a spherical wall 131, defined by a spherically curved inner wall 132 and a similarly shaped spherical outer wall 133, extending between a closed end 134 of the cap 120 and the cylindrical wall 122. The spherical inner wall 132 defines a section of a sphere in a manner similar to that described for the spherical inner wall 32 of the site cover 10. The inner wall 132 terminates at an intersection or junction with the cylindrical inner surface 124. The area of the inner cavity 130 surrounded by the cylindrical inner wall 124 comprises a first chamber 138 of the inner cavity 130, and the area of the inner cavity 130 surrounded by the spherical inner wall 132 comprises a second chamber 140 of the inner cavity 130.

It may be noted that the diameter of the curved inner wall 132 of the site cover 110 is greater than that illustrated for the site cover 10 described above, and may therefore include a larger diameter spherical compressible member 142 (absorbent material) containing a greater quantity of disinfectant solution. Further, by providing the spherical wall 131, the site cover 110 can provide a reduced resistance to squeezing or compression for dispensing the disinfectant solution contained in the compressible member 142, thereby further facilitating dispensing of the solution. The placement and dispensing operation of the site cover 110 on the site 112 can be performed in a manner substantially similar to that described above for the site cover 10 on the site 12.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A medical site cover for a needle-free intravenous connector having a septum area and external threads, the medical site cover comprising:
   a cap having an opening to an inner cavity;
   the inner cavity including a first chamber adapted for receiving and surrounding the connector and a second chamber located between the first chamber and a closed end of the cap; and
   a compressible member formed of an absorbent material located in the second chamber, the compressible member being a sphere;
   wherein the second chamber is configured with a curved wall defining a section of a sphere having a radius that is the same as a radius of the compressible member.

2. The medical site cover of claim 1, including a disinfectant agent in the absorbent material.

3. The medical site cover of claim 1, including a lip formed at an inner end of the first chamber, the lip defining a diameter that is less than a diameter of the first chamber and the second chamber terminates at the lip.

4. The medical site cover of claim 3, wherein the compressible member includes a portion, defined by a continuation of the sphere, that extends past the lip into the first chamber.

5. The medical site cover of claim 1, wherein the second chamber has a volume that is greater than $(4/6)\pi r3$ where r is the radius of the compressible member.

6. The medical site cover of claim 1, wherein the cap is formed of an elastomeric material.

7. The medical site cover of claim 6, wherein the first chamber is defined by an inner wall of the cap that is smooth for engaging in deforming contact around external threads on a connector.

8. The medical site cover of claim 6, wherein the cap is flexible to elastically deform the second chamber and the compressible member by application of an elastic deformation force on an outer surface of the cap.

9. The medical site cover of claim 6, including a rib extending circumferentially on an outer surface of the cap at a location adjacent to the opening to the inner cavity, wherein the rib defines a maximum dimension of the cap in a direction perpendicular to the opening.

10. The medical site cover of claim 6, wherein an outer surface of the cap surrounding the first chamber is cylindrical and an outer surface of the cap surrounding the second chamber is spherical.

11. A medical site cover for a needle-free intravenous connector having a septum area and external threads, the medical site cover comprising:
    a cap formed entirely of an elastomeric material, the cap having an opening to an inner cavity;
    the inner cavity including a first chamber defined by a smooth inner wall adapted for receiving and surrounding the connector and a second chamber located between the first chamber and a closed end of the cap;
    a lip formed at an inner end of the first chamber, the lip defining a diameter that is less than a diameter of the first chamber, and the second chamber terminates at the lip wherein the second chamber has at least one diameter greater than the diameter of the lip;
    a compressible member formed of an absorbent material located in the second chamber, the compressible member being a sphere; and
    a disinfectant agent in the absorbent material;

wherein the compressible member includes a portion, defined by a continuation of the sphere, that extends into the first chamber.

12. The medical site cover of claim 11, wherein the second chamber is configured with a curved wall defining a section of a sphere having a radius that is the same as a radius of the compressible member.

13. The medical site cover of claim 12, wherein the curved wall terminates at a junction between the second chamber and the first chamber.

14. The medical site cover of claim 12, wherein the second chamber has a volume that is greater than $(4/6)\pi r3$ where r is the radius of the compressible member.

15. The medical site cover of claim 11, wherein the cap is flexible to elastically deform the second chamber and the compressible member by application of an elastic deformation force on an outer surface of the cap.

16. The medical site cover of claim 11, including a rib extending circumferentially on an outer surface of the cap at a location adjacent to the opening to the inner cavity, wherein the rib defines a maximum dimension of the cap in a direction perpendicular to the opening.

17. The medical site cover of claim 11, wherein an outer surface of the cap surrounding the first chamber is cylindrical and an outer surface of the cap surrounding the second chamber is spherical.

18. A medical site cover for engaging a Luer connector having a housing supporting a septum with an exposed surface for receiving a male Luer and having external threads, the medical site cover comprising:

a cap having an opening to an inner cavity;

the inner cavity including a first chamber adapted for receiving and surrounding the housing and a second chamber located between the first chamber and a closed end of the cap; and a compressible member having an uncompressed curved outer surface and formed of an absorbent material located in the second chamber, the curved surface of the compressible member extending in the second chamber;

wherein the second chamber is configured with an inner wall defining the closed end of the cap, and the curved surface of the compressible member includes a portion that extends into contact with the inner wall within the second chamber and further includes a portion curving outward opposite from the inner wall of the second chamber into the first chamber for engagement of the curved surface with the septum surface of a Luer connector within the first chamber.

19. The medical site cover of claim 18, wherein at least half of the compressible member is located in the second chamber.

20. The medical site cover of claim 19, wherein the cap is formed of an elastomeric material and the first chamber is defined by an inner wall of the cap that is smooth for engaging in deforming contact around external threads on a connector.

21. The medical site cover of claim 19, wherein the cap is formed of an elastomeric material to elastically deform the second chamber and the compressible member by application of an elastic deformation force on an outer surface of the cap.

22. The medical site cover of claim 18, including a lip formed at an inner end of the first chamber, the lip defining a diameter that is less than a diameter of the first chamber, and the second chamber terminates at the lip.

* * * * *